United States Patent [19]

Sutton, Jr. et al.

[11] Patent Number: 5,315,234
[45] Date of Patent: May 24, 1994

[54] EDDY CURRENT DEVICE FOR INSPECTING A COMPONENT HAVING A FLEXIBLE SUPPORT WITH A PLURAL SENSOR ARRAY

[75] Inventors: George H. Sutton, Jr.; Francis H. Little, both of Cincinnati, Ohio; Kristina H. V. Hedengren; Richard J. Charles, both of Schenectady, N.Y.; William P. Kornrumpf; Donna C. Hurley, both of Albany, N.Y.

[73] Assignee: General Electric Company, Cincinnati, Ohio

[21] Appl. No.: 862,950

[22] Filed: Apr. 3, 1992

[51] Int. Cl.⁵ .................. G01N 27/82; G01R 33/12; H01F 21/02
[52] U.S. Cl. ............................ 324/242; 324/232; 324/262; 336/200
[58] Field of Search ............ 324/234, 236, 237–243, 324/260–262, 219–221; 336/20, 200

[56] References Cited

U.S. PATENT DOCUMENTS

| 2,622,125 | 12/1952 | Bender | 324/220 |
| 4,543,528 | 9/1985 | Baraona | 324/262 |
| 4,593,245 | 6/1986 | Viertl et al. | 324/262 X |
| 4,668,912 | 5/1987 | Junker | 324/220 |
| 4,719,422 | 1/1988 | deWalle et al. | 324/238 |
| 5,023,549 | 6/1991 | Dau et al. | 324/262 X |
| 5,047,719 | 9/1991 | Johnson et al. | 324/242 |

FOREIGN PATENT DOCUMENTS

| 152687A1 | 8/1985 | European Pat. Off. |
| 231365A2 | 8/1987 | European Pat. Off. |
| 423753A1 | 4/1991 | European Pat. Off. |
| 450950A2 | 10/1991 | European Pat. Off. |

OTHER PUBLICATIONS

S. Oaten and J. Bertelle, "Robot Controlled Inspection of Roto-Symmetrical Parts", 1992 ASNT Spring Conference, NDE-The Vehicle to the Future, pp. 117–119.
Patent Abstracts of Japan, vol. 16, No. 52(E-1164) 10 Feb. 1992 & JP-A-32 54 103 (Kawasaki) 13 Nov. 1991, Abstract.
Database WPI, Week 9002, Derwent Publications Ltd., London, GB; AN 90-008592 & DE-A-39 19 976 (Nippon Antenna) 28 Dec. 1989, Abstract.

Primary Examiner—Gerard R. Strecker
Assistant Examiner—Warren S. Edmonds
Attorney, Agent, or Firm—Charles L. Moore, Jr.; Jerome C. Squillaro

[57] ABSTRACT

An eddy current device for inspecting a component includes an eddy current array circuit having respective pluralities of drive and sense elements and having an active face for positioning on a surface of the component during the inspection operation. A backing is disposed on a face of the eddy current array circuit opposite to the active face for concentrating an electromagnetic flux from the eddy current array circuit into the component when each of the plurality of drive elements is being energized. A mechanical arrangement is provided for supporting and deploying the backing and the array circuit to substantially conform with the surface portion under inspection and to cause each of the pluralities of drive and sense elements to be maintained at their respective substantially constant distances from the inspection surface during scanning, preferably at a controlled rate of scan.

35 Claims, 12 Drawing Sheets

EDDY CURRENT DEVICE FOR INSPECTING A
COMPONENT HAVING A FLEXIBLE SUPPORT
WITH A PLURAL SENSOR ARRAY

RELATED APPLICATIONS

The present application is related to the following patent applications:

Co-pending patent application Ser. No. 07/696,455, entitled "Eddy Current Probe Arrays" by Kristina H. Hedengren et al., which discloses and claims a plurality of spatially correlated eddy current probe elements sufficiently disposed within a flexible interconnecting structure to collect a discrete plurality of spatially correlated eddy current measurements for nondestructive near surface flaw detection. This application is assigned to the same assignee as the present application and is incorporated herein in its entirety by reference.

Co-pending patent application Ser. No. 07/696,456, entitled "Method and Apparatus for Nondestructive Surface Flaw Detection" by John D. Young et al., which discloses and claims a method and apparatus for acquiring a plurality of synchronized, spatially correlated, discrete eddy current measurement signals for image processing. This patent application is also assigned to the same assignee as the present application and is incorporated herein by reference in its entirety.

Co-pending patent application Ser. No. 07/696,457, now U.S. Pat. No. 5,237,271 entitled: "Multi-Frequency Eddy Current Sensing" by Kristina H. Hedengren, which discloses and claims a method for improving resolution and characterization in detection of near surface flaws using non-destructive eddy current inspection. This patent application is also assigned to the same assignee as the present application and is incorporated herein by reference in its entirety.

Co-pending patent application Ser. No. 07/504,769, now abandoned entitled "A Flexible High Density Interconnect Structure and Flexibly Interconnected System" by Charles W. Eichelberger, et al., which describes a multi-layer multi-component integrated fabrication technology suitable for making flexible, spatially correlated, eddy current probe arrays for inspecting surfaces which have complex geometric shapes. This co-pending application is also assigned to the same assignee as the present application and is incorporated herein by reference in its entirety.

Patent application Ser. No. 07/862,699, now U.S. Pat. No. 5,262,722, entitled "Apparatus for Near Surface Nondestructive Inspection Scanning of a Conductive Part" by Kristina H. Hedengren, et al., filed concurrently herewith, which describes an ultra-thin, flexible, film-like, multi-layer eddy current probe array structure which is configured to provide electrical and mechanical interconnection to respective system electronics and mechanical scanning means. This related application is also assigned to the same assignee as the present application and is incorporated herein by reference in its entirety.

BACKGROUND OF THE INVENTION

The present invention relates to the inspection of components using eddy current technology and, more particularly, to a device for inspecting a component having a complex geometric shape, such as a dovetail slot, gear tooth or the like of a gas turbine engine component or similar workpiece using a multiplicity of eddy current probe or circuit elements formed in an array to provide inspection of a larger surface area in a shorter time than has heretofore been available with a substantially lower probability of missing a flaw or defect.

Eddy current inspection is a commonly used technique for detecting discontinuities or flaws in the surface of components such as the components of a gas turbine engine. Eddy current techniques are based on the principle of electromagnetic induction in which eddy currents are induced within the component under inspection. The eddy currents are induced in the component by alternating magnetic fields created in a coil of an eddy current probe, referred to as a drive coil, when the probe is moved into proximity with the component under inspection. Changes in the flow of eddy currents are caused by the presence of a discontinuity or a crack in the test specimen. The altered eddy currents produce a secondary magnetic field which is received by the eddy current probe coil or by a separate sense coil in the eddy current probe which converts the altered secondary magnetic field to an electrical signal which may be recorded on a strip chart or similar device for analysis. An eddy current machine operator may then detect and size flaws by monitoring and analyzing the recorded signals. Flaws or defects are detected if the electrical signal exceeds a predetermined voltage threshold.

Referring to FIG. 1, a present method of inspecting a component 10, such as a dovetail slot of a rotor, spool or disk of a gas turbine engine, as shown in FIG. 1, uses a single eddy current probe which will typically have two coils connected in a bridge circuit for simultaneous driving and sensing. The single eddy current probe 12 is moved linearly, as indicated by arrow 14 across the interior surface 16 of dovetail slot 18 to scan the surface and detect any flaws or defects present therein. After a complete scan across interior dovetail slot surface 16 in direction 14, the single eddy current probe 12 is indexed or incrementally moved to a next scan location 12' as shown in phantom in FIG. 1. The probe at location 12' is then scanned again across the interior surface 16 of dovetail slot 18. This systematic process of scanning and indexing the single probe 12 is repeated until the entire interior surface 16 of dovetail slot 18 desired to be inspected has been scanned. This single probe/line scan procedure typically requires an extended period of time to substantially completely and adequately inspect the desired surface area even for relatively small dovetail slots and will take even longer as the slot size increases for larger disks and rotors. Additionally, the eddy current probe 12 must be carefully indexed each time so that no area and any small flaws within this area will be missed.

SUMMARY OF THE INVENTION

It is, accordingly, a primary object of the present invention to provide a novel apparatus for inspecting a component which is not subject to the foregoing disadvantages.

It is another object of the present invention to provide a novel device for inspecting a component which will substantially completely scan a selected area under inspection with minimal or no indexing and without any voids or areas which are missed during the scanning.

It is a further object of the present invention to provide a novel device for inspecting a dovetail slot, gear tooth or the like of a gas turbine engine component in a single pass with the eddy current probe elements being maintained at a substantially constant equal distance from the surface under inspection during the entire scan.

In accordance with the present invention, a device for inspecting a component, including a component having a complex geometric shape, includes an eddy current array circuit having respective pluralities of drive and sense elements and having an active face for positioning on a surface portion of the component during inspection. A backing is disposed on a face of the eddy current array circuit which is opposite to the active face of the array to support the array circuit against a component surface during an inspection operation. In some applications the backing may be made of a magnetic or soft ferrite composite material for concentrating an electromagnetic flux from the eddy current array circuit into the component under inspection when each of the plurality of drive elements or coils is being energized by an external power source. Additionally, the ferrite backing would shield the eddy current array circuit from any extraneous electromagnetic energy. Means for supporting and deploying the compliant backing and the eddy current array circuit cause the backing and array circuit to conform to the surface portion of the component under inspection and cause each of the pluralities of the drive and sense elements to be maintained at their respective constant distances from the component surface portion under inspection during a scanning operation wherein the device is moved across the inspection surface.

In accordance with one embodiment of the present invention, the supporting and deploying means is a core of a rigid material which is shaped to substantially conform with the surface of the component under inspection.

In another embodiment of the present invention, the core material is compressible to provide a close uniform fit between the flexible eddy current array circuit and the surface of the component under inspection so as to accommodate different sizes of inspection surfaces, such as different size dovetail slots or the like.

In yet a further embodiment of the present invention, the supporting and deploying means includes a forming bar and may also include a locating bar for positioning the eddy current array probe within a dovetail slot or the like and to cause the eddy current array circuit to conform to the component surface under inspection when the forming bar and locating bar, if necessary, are deployed to their respective inspection positions.

These and other objects of the invention, together with features and advantages thereof, will become apparent from the following detailed specification when read with the accompanying drawings in which like reference numerals refer to like elements.

DETAILED DESCRIPTION OF THE PREFERRED EMBODIMENTS

The present invention will be described with respect to inspecting a dovetail slot of a gas turbine engine rotor, disk or the like; those skilled in the art, however, will recognize that the principles of the present invention could be easily adapted or modified to inspect any component having a simple or complex geometric surface.

Figure 1:
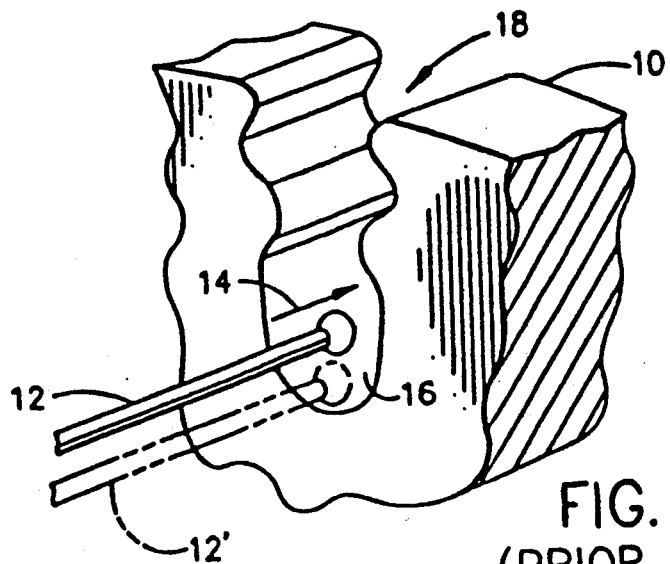
FIG. 1 is an illustration of a prior art single probe/line scan device for inspecting a dovetail slot of a gas turbine engine component.
Figure 2:
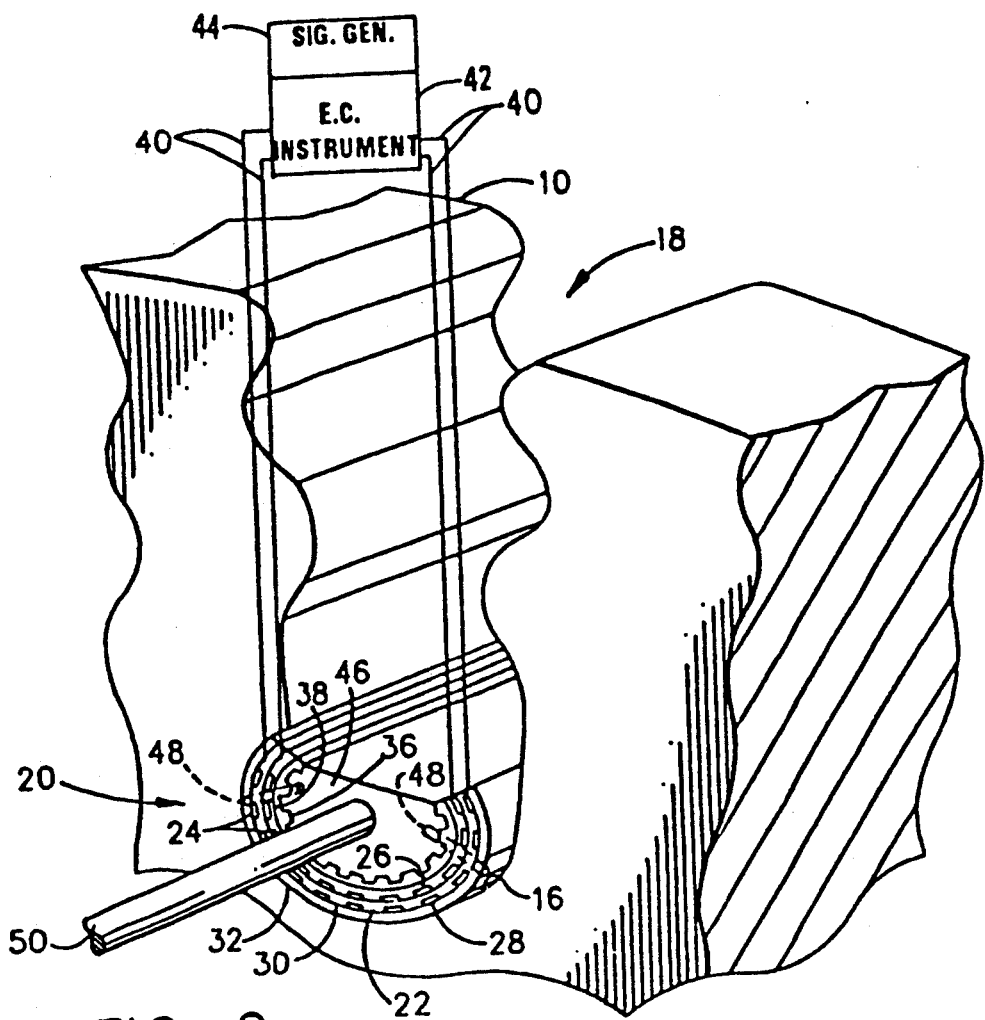
FIG. 2 is an eddy current array probe device for inspecting the bottom portion of a dovetail slot of a gas turbine engine in accordance with the present invention.

Referring initially to FIG. 2, a device 20 for inspecting a dovetail slot 18 of a gas turbine engine, a gear tooth or similar complex geometric surface includes a flexible eddy current array circuit 22, such as those described in co-pending U.S. patent application Ser. No. 07/696,455, entitled "Eddy Current Probe Arrays". Array circuit 22 is an integrated, microelectronic constituent including a plurality of miniaturized, sufficiently distributed eddy current circuit elements, as illustrated by small blocks 24 in FIG. 2. Circuit elements 24 are electrically conductive coils which are fabricated within a flexibly conforming structure using High Density Interconnect (HDI) precision processing, as described in co-pending application Ser. No. 07/504,769, now abandoned entitled "A Flexible High Density Interconnect Structure and Flexibly Interconnected System". Typically, the elements 24 are made up of two functionally different and insulatively separated sets of electrical coils, drive coils 26 for inducing the electromagnetic field in the component 10 under inspection and a second set of sense coils 28 for detecting any change in the induced electromagnetic field which may be caused by any flaw present in the surface 16 of the component 10. The drive coils 26 and sense coils 28 may be disposed in separate layers of passivation material as shown in FIG. 2 or they may be configured to reside in the same layer. The flexible eddy current array circuit 22 has an active face 30 for positioning against the component surface portion 16 during an inspection operation. A protective or sacrificial layer 32 of material, such as Kapton TM or Teflon TM, may be disposed over active face 30 to protect the array circuit 22 as it is moved along or scans the surface portion 16 under inspection and to facilitate sliding the active face 30 along the surface portion 16. A backing layer 36, which may be a flexible, compliant material, is disposed on a face 38 of array circuit 22 opposite to active face 30 to support the array circuit against the component surface portion 16 during an inspection operation. The backing layer 36 may be made of a ferrite containing material to concentrate an electromagnetic flux from the drive coils 26 into the component when each of the drive coils 26 are energized. Suitable electrical conductors and connectors shown schematically by lines 40 are provided for electrically connecting the drive coils 26 and sense coils 28 to an eddy current instrument 42. Electrical connection of the drive and sense coils 26 and 28 is described in more detail in U.S. patent application Ser. No. 07/862,699, now U.S. Pat. No. 5,263,722 entitled "Apparatus for Near Surface Nondestructive Inspection Scanning of a Conductive Part".

Eddy current instrument 42 may include electronic circuitry (not shown) such as that described in co-pending U.S. patent application Ser. No. 07/696,456, now U.S. Pat. No. 5,182,513, entitled: "Method and Apparatus for Nondestructive Surface Flaw Detection" and co-pending U.S. patent application Ser. No. 07/696,457, now U.S. Pat. No. 5,237,271, entitled: "Multi-Frequency Eddy Current Sensing" for receiving the signals from sense coils 28 and for converting the signals to images for the detection of flaws or defects in surface portion 16. Eddy current instrument 42 may also include a signal generator 44 for energizing drive coils 26. Signal generator 44 may also be a separate device from instrument 42.

The flexible backing 36 may be a magnetic ferrite material including about 50% to about 60% by volume soft ferrite particulates bonded by an organic elastomer, preferably a polyurethane rubber, and has a substantial relative magnetic permeability, preferably a relative permeability of about 4 or more. An example of a ferrite compound which may be used in particulate form includes about 37% MnO, about 9% ZnO and about 54% $Fe_2O_3$ by molar composition. While the flexible compliant array backing 36 has been described as being made from a ferrite material, it is also within the comprehension of the present invention that the flexible compliant array backing and the flexible ferrite for directing or concentrating the electromagnetic flux from the drive coils 26 into the component 10 can be separate layers of material.

The flexible, compliant eddy current array circuit 22 and the compliant backing 36 may have anisotropic mechanical properties to facilitate formation of the array circuit 22 and backing 36 about a core 46 and in compliance with the shape of the core 46. The core 46 may be a rigid material, such as a hard engineering plastic or the like and may be molded or shaped to conform with the desired shape of the surface of the component to be inspected. The core 46 may also be made from a compressive material, such as an elastomer or the like to provide a close fit to the inspection surface.

The eddy current array probe device 20 may be fabricated by placing the flexible eddy current array circuit 22 into a mold which is made to accurately fit the intended inspection surface. Proper alignment or registration of the probe elements 24 with the backing 36 and core material 46 may be provided by registration holes 48, shown in phantom, through which pins may be inserted during the molding process. The core 46 is then molded inside the flexible array circuit 22 to provide a conformable probe 20.

A suitable handle 50 or similar scanning arrangement may be provided to facilitate movement of the array probe device 20 across the inspection surface 16 to scan the surface, preferably at a controlled rate of scan for any defects. The handle 50 may be a push rod connected to an electrical motor, a pneumatic piston or other mechanical device to move the array probe device 20 across the inspection surface 16.

Figure 3:
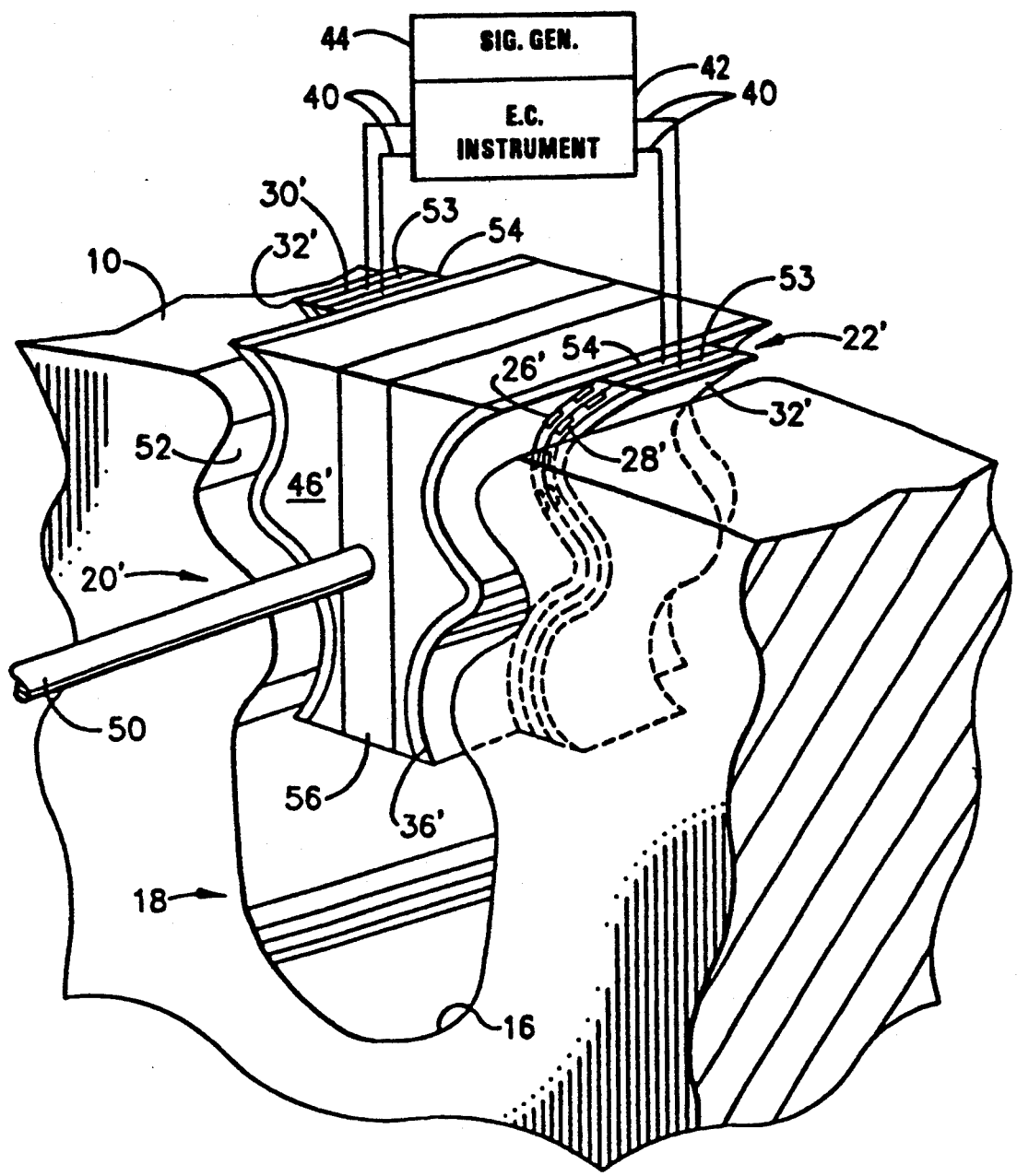
FIG. 3 is an eddy current array probe device for inspecting an intermediate surface portion of a dovetail slot of a gas turbine engine.

Referring to FIG. 3, in accordance with another embodiment of the present invention, an eddy current array probe device 20' for inspecting an upper interior surface portion 52 of a dovetail slot 18 includes a flexible, compliant eddy current array circuit 22' similar to that of array probe device 20. The flexible eddy current array circuit 22' comprises a first layer 53 of material having a plurality of sense coils 28' formed thereon using HDI process technology and a second layer 54 of material having a plurality of drive coils 26' formed thereon. A sacrificial layer 32' may also be disposed on an active face 30' of array circuit 22' and a flexible, compliant backing layer 36', which may be of a ferrite material, is disposed between second layer 54 and the probe core 46'. Probe core 46' may be a rigid material, such as an engineering plastic or the like, which is specifically molded and shaped to conform to the shape of the surface portion 52 under inspection with the eddy current array circuit 22' and backing 36' attached thereto and also conforming to the shape of core 46'. An inner core 56 of a compressible material may be provided to maintain a close fit to the inspection surface portion 52 and to prevent the creation of a space between the device 20' and the inspection surface portion 52 during scanning of the surface for detection of flaws or liftoff as it is known in the industry; thereby the drive coils 26' and sense coils 28' are maintained at a constant uniform distance from the inspection surface 52 during scanning by the eddy current array probe device 20'. The device 20' is preferably moved or scanned across the inspection surface 52 by handle 50 at a controlled rate of scan.

An additional embodiment of the present invention would be to form core 46' and inner core 56 integrally from a compressible material, such as an elastomer or the like, to provide the close fit to the inspection surface portion 52 and to prevent liftoff during an inspection operation.

It is also within the comprehension of the present invention that the eddy current array probe device 20 of FIG. 2 and device 20' of FIG. 3 could be integrally formed together on a single handle 50; one limitation to such a combination would be the eddy current signal acquisition electronics, such as the apparatus described and claimed in co-pending U.S. patent application Ser. No. 07/696,456 (U.S. Pat. No. 5,182,513) and co-pending U.S. patent application Ser. No. 07/696,457 (U.S. Pat. No. 5,237,271).

Figure 4:
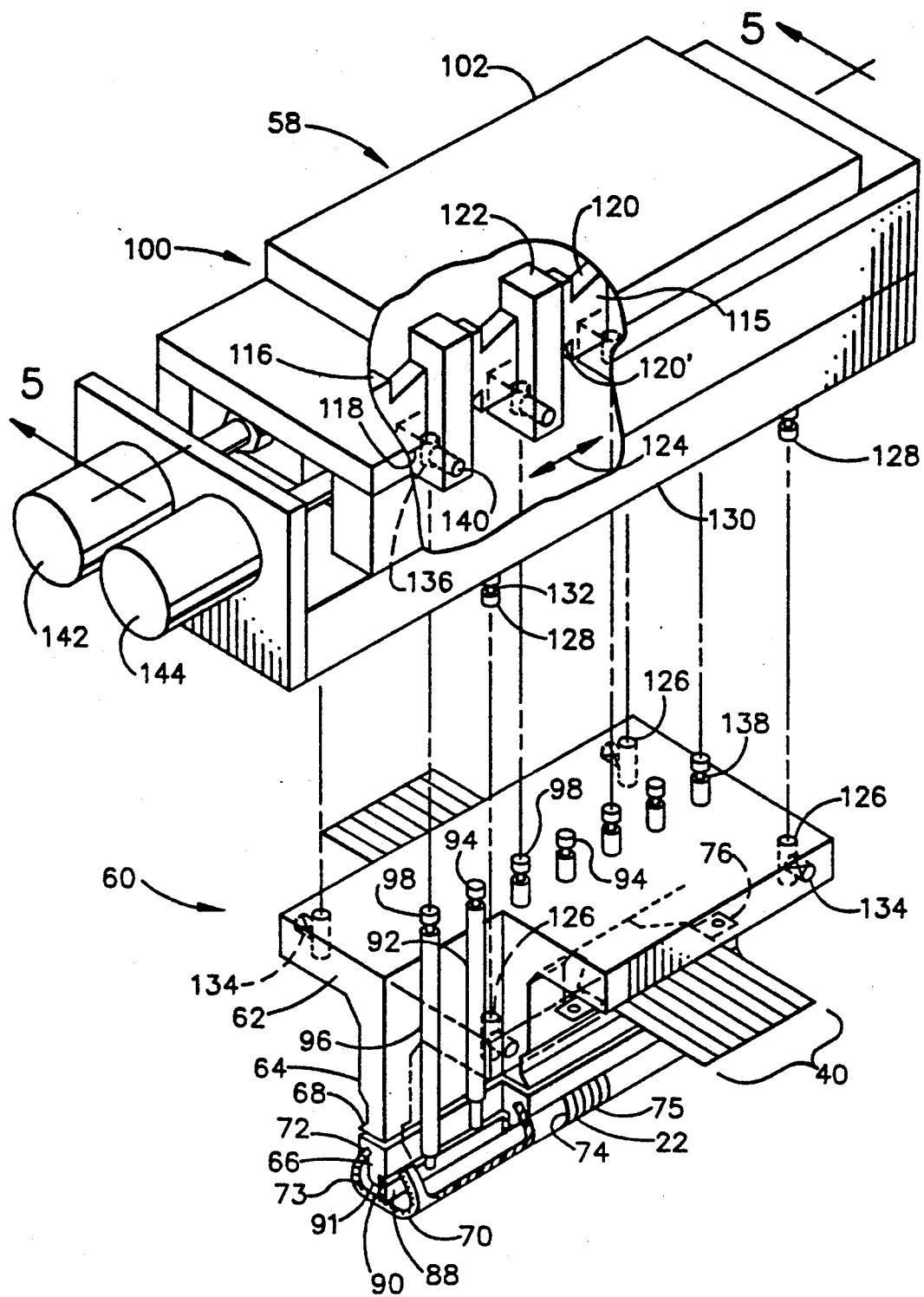
FIG. 4 is an exploded perspective view of an alternate embodiment of the present invention.

Referring to FIG. 4, a further embodiment of the present invention includes a device 58 for inspecting a complex geometric surface, such as the interior surface of a dovetail slot of a gas turbine engine or the like. Array probe device 58 includes a guide body 60 with a guide body base 62 and a guide body probe extension member 64 extending substantially perpendicular to the guide body base 62. A forming bar 66 is positioned at an end 68 of probe extension member 64 and is movable between a retracted position against the extension member 64 and an inspection position at a spacing from the extension member 64. A flexible, compliant backing 70 is disposed over forming bar 66 and is captured within recesses 72 formed in the outer edges of forming bar 66 to secure the backing over forming bar 66. Compliant backing 70 may have a plurality of ridges 73 formed thereon, which extend substantially parallel to the longitudinal extent of the forming bar 66 and parallel to the intended direction of scan across an inspection surface, to facilitate disposition of compliant backing 70 over the forming bar 66 and to permit the compliant backing 70 to conform to any surface under inspection. The ridges 73 also provide support to prevent the backing 70 from lifting off the surface under inspection as the guide body 60 is moved in the direction parallel to the ridges 73 along a surface for inspection thereof.

A flexible, compliant eddy current array circuit 22 is disposed over backing 70. A plurality of electrical conductors 74 and 75 for making respective electrical contact between the drive and sense coils 26 and 28 (not shown in FIG. 4 for purposes of clarity) and the eddy current electronics (not shown) extend up both sides of guide body extension member 64 and extend out beyond the edges of guide body base 62 to provide means for connecting the array circuit elements to the eddy current system electronics or instrumentation similar to that described with respect to FIGS. 2 and 3. The array circuit 22 is held in proper position or registration with respect to the guide body 60 by brackets 76 mounted on both sides of guide body base 62 (bracket 76 is only shown on one side of guide body base 62 for purposes of explanation).

Figure 6:
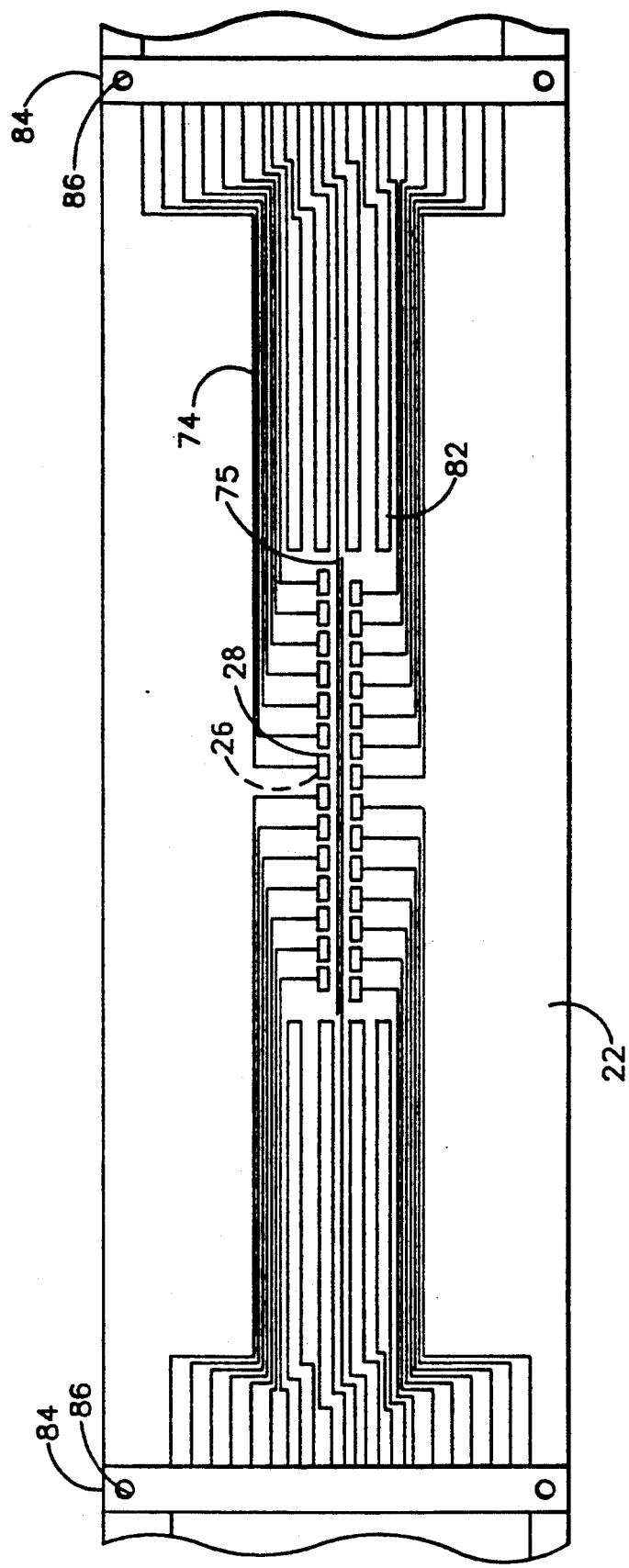
FIG. 6 is a schematic diagram illustrating an example of an eddy current array circuit in accordance with the present invention.
Figure 7:
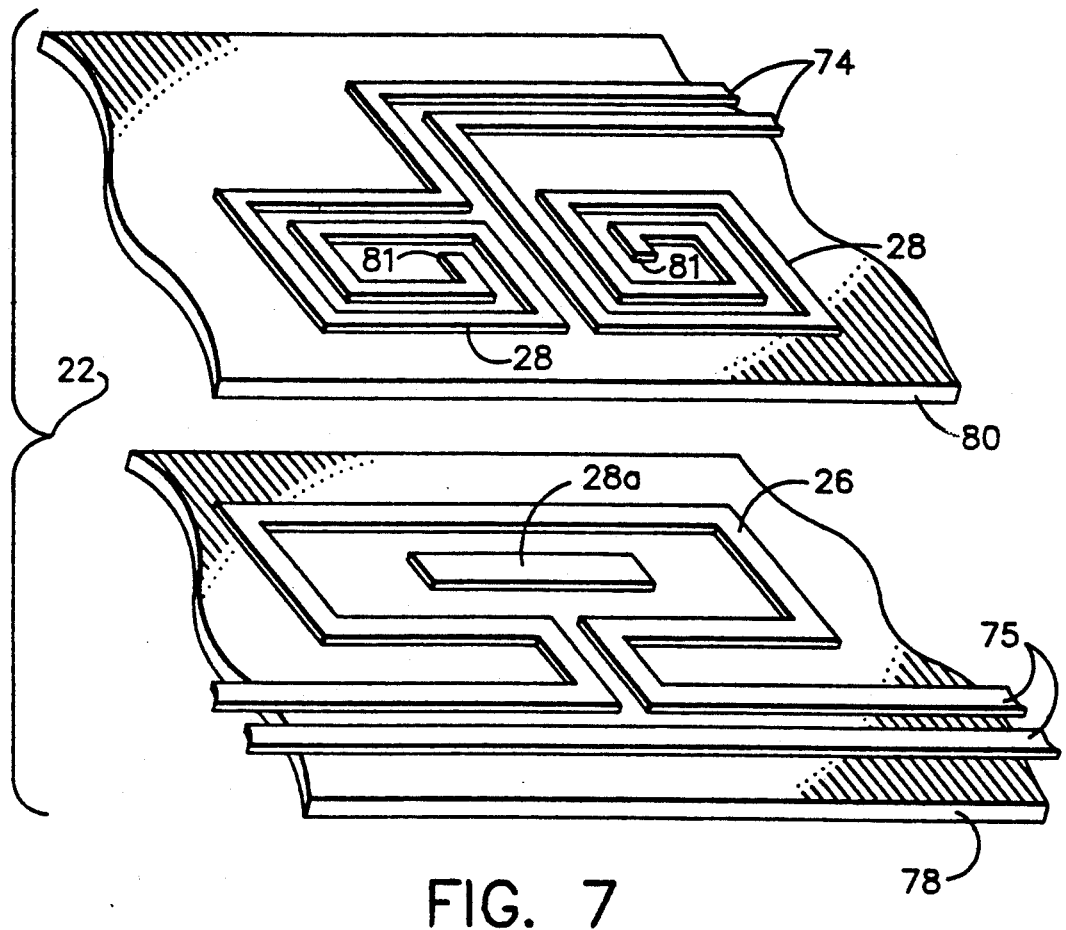
FIG. 7 is a detailed exploded perspective view of a single pair of drive and sense coils or elements of the array circuit of FIG. 6.

Eddy current array circuits and electrical and mechanical interconnection means of the type which may be used with device 58 are described in U.S. patent application Ser. No. 07/862,699 (5,262,722), entitled "Apparatus for Near Surface Nondestructive Inspection Scanning of a Conductive Part". Briefly described, an example of an eddy current array circuit 22 which may be used with the device 58 is shown schematically in FIG. 6. The drive coils 26 and sense coils 28 may be disposed one above the other in different flexible layers or substrates 78 and 80 as best shown in FIG. 7. The substrates 78 and 80 are shown separated in an exploded perspective view in FIG. 7 for purposes of clarity and explanation. Holes or vias 81 are formed through the substrate 80 for electrically interconnecting the sense coils 28 by a shorting strip 28a disposed on the other substrate 78. Those skilled in the art will recognize that the coils 26 and 28 could also be configured to reside in the same layer or substrate. Electrical contact is made between drive coils 26 and the eddy current electronics by conductors 75 and electrical contact is made between sense coils 28 and the eddy current electronics by conductors 74. Both conductors 74 and 75 are brought out to the outer edge of the substrates 78 and 80 of eddy current array circuit 22 to provide means for connecting the flexible array circuit 22 to the system electronics. As shown in FIG. 6, conductive shielding strips 82 may be disposed between drive lines 75 and sense lines 74 to provide electromagnetic shielding between the conductive lines. Registration plates 84 (FIG. 6) may be provided to mate with brackets 76 to secure the array circuit 22 to the guide body 60 and to ensure proper registration of the electrical conductors 74 and 75 to the electrical wiring 40 (FIG. 4) for connection to the system electronics (not shown in FIG. 4). Registration holes 86 may also be provided or may be provided in place of registration plates 84 to secure array circuit 22 to guide body 60 and to provide proper registration of the electrical conductors 74 and 75 to electrical wiring 40.

Referring back to FIG. 4, the flexible, compliant backing 70 may be made from a ferrite material or another layer of ferrite material may be disposed between the array circuit 22 and the backing 70 to concentrate the electromagnetic flux from the drive elements or coils 26 into the component under inspection. As previously discussed, the ferrite material is a soft ferrite and preferably has a relative permeability of 4 or more.

A locating bar 88 may be positioned within a recess 90 formed in an end or operating face 91 of forming bar 66 opposite to guide body extension member 64. Locating bar 88 may be required for the inspection of some larger dovetail slots to provide proper orientation of the eddy current array circuit 22 within the dovetail slot in those situations where the forming bar 66 alone cannot adequately perform this function to provide repeatable and comparable inspection results between different components or surfaces.

Figure 5:
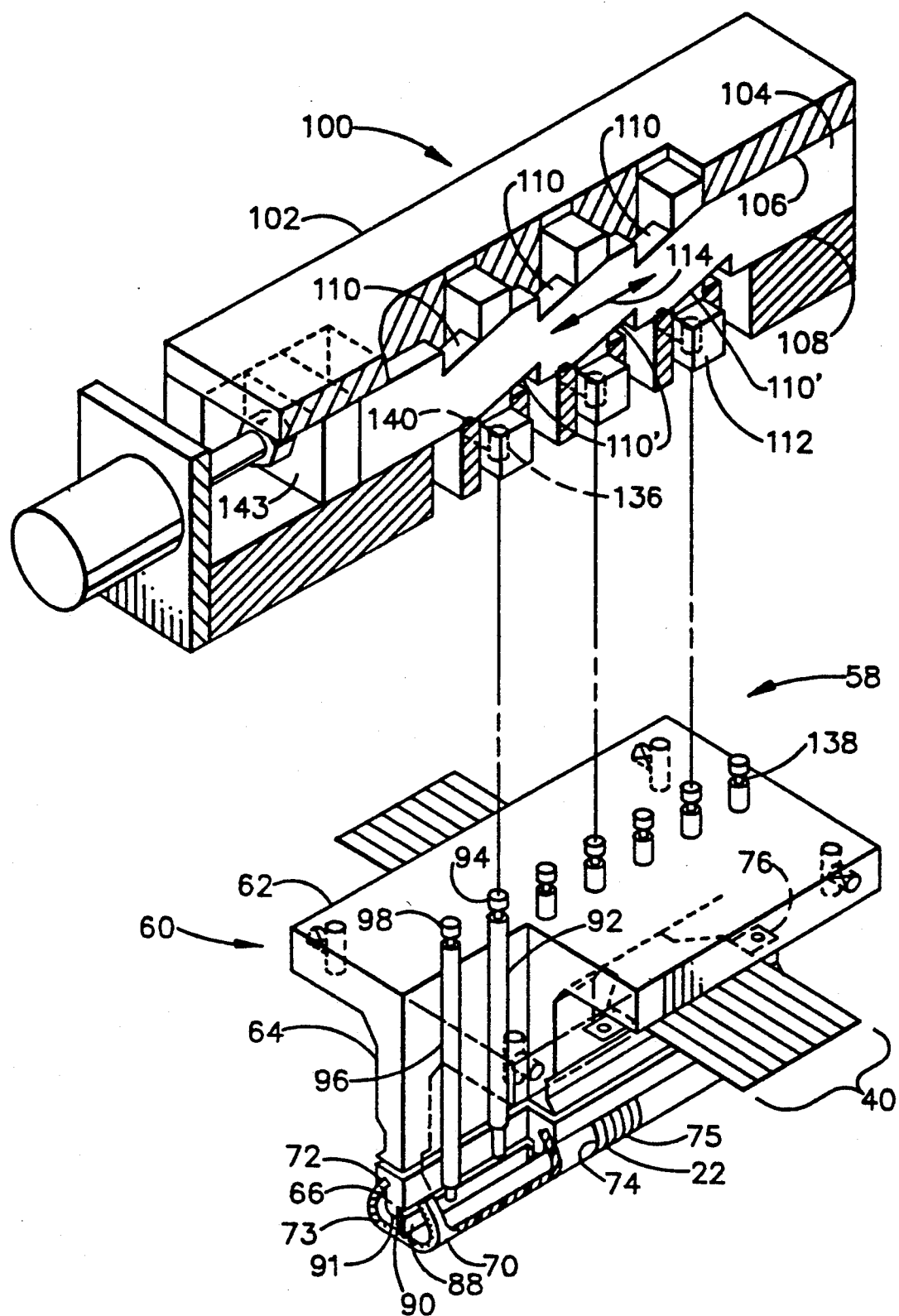
FIG. 5 is a perspective cross-sectional view of the device shown in FIG. 4 taken along lines 5—5.

Referring also to FIG. 5, a plurality of channels 92 is formed through guide body 60 and one of a plurality of forming pins 94 are respectively received in and extend through each of channels 92 and are each coupled to the forming bar 66. If a locating bar 88 is also provided, a second plurality of channels 96 is formed through guide body 60 and one of a plurality of locating pins 98 are respectively received in each of the channels 96, extend through each of the channels 96 and are each coupled to the locating bar 88.

In accordance with the present invention, an actuator arrangement 100 is provided for extending and retracting each of the plurality of forming pins 94 to cause the forming bar 66 to move between a retracted position and an inspection position. In those situations where a locating bar 88 is not necessary, the forming bar 66 provides proper positioning of the array circuit 22 at substantially the same location relative to the dovetail slot surface under inspection when the forming bar 66 is in its inspection position at a spacing from extension member 64. The forming bar 66 also causes the array circuit 22 to conform to the shape of the surface under inspection, when the forming bar 66 is in the inspection position, and the forming bar 66 also maintains each of the plurality of drive elements 26 and sensing elements 28 at their respective constant equal distances from the dovetail slot surface during the inspection operation. If a locating bar 88 is necessary, the actuator 100 also controls extension and retraction of locating pins 98 to cause locating bar 88 to move between a retracted position at least partially withdrawn within recess 90 and a locating position extending from the end or operating face 91 of forming bar 66.

Actuator arrangement 100 includes a housing 102 as shown in FIG. 5. An elongated forming gib 104 is slidably mounted within the housing 102 and has a pair of substantially saw-tooth shaped surfaces 106 and 108 on opposite sides thereof to form a plurality of paired, inclined surface portions 110 and 110' along the elongated extent of gib 104. A plurality of substantially C-shaped forming pin operating members 112 are each respectively disposed about one of the paired, inclined surface portions 110 and 110' and each C-shaped forming pin operating member 112 is respectively coupled to one of the plurality of forming pins 94 to cause each of the forming pins 94 to extend and retract when the forming gib 104 is respectively slid in one direction corresponding to its elongated extent or in the opposite direction, as indicated by double arrow 114 in FIG. 5.

If the locating bar 88 is provided, then actuator 100 includes a second gib or locating gib 115 (FIG. 4) positioned adjacent forming gib 104. The second locating gib is similarly shaped including saw-tooth surfaces 116 and 118 which form paired, inclined surface portions 120 and 120'. A plurality of substantially C-shaped locating pin operating members 122 are each respectively disposed about one of said paired, inclined surface portions 120 and 120'. Each locating pin operating member 122 is respectively coupled to one of the plurality of locating pins 98 to cause each of the locating pins 98 to extend and retract when the locating gib 115 is respectfully slid in one direction corresponding to its elongated extent and in an opposite direction, as indicated by double arrow 124 in FIG. 4.

Probe guide body 60 and actuator 100 are designed to permit easy attachment to one another and detachment from one another to facilitate using actuator 100 with different types of probes for inspection of different surfaces. Guide body base 62 has a plurality of recesses or holes 126 formed therein for receipt of alignment pins 128 extending from a base 130 of actuator 100. Each of alignment pins 128 may have a groove 132 formed therein which is captured by a spring biased piston 134 mounted in probe guide body base 60 and extending partially into alignment hole 126. Another means for connecting the guide body 60 and the actuator 100 is to form threaded holes or recesses in either the guide body 60 or the actuator 100 and to attach the two components using thumb screws. Such quick connect and disconnect arrangements are known.

Each of forming pin operating members 112 and locating pin operating members 122 also have a recess or hole 136 formed therein for respective receipt of an end of the forming and locating pins 94 and 98 extending from guide body base 62. Each of forming and locating pins 94 and 98 have a concentric groove 138 formed therein which is releasably captured by a spring biased piston 140 mounted within each of pin operating members 112 and 122 and which extends partially into the recess 136 to releasably engage groove 138 when each of pins 94 and 98 are received within recesses 136. Thus, spring biased pistons 134 and 140 are designed to respectively release alignment pins 128 and forming and locating pins 94 and 98 when pressure is applied to separate probe guide body 60 from actuator 100 for attachment of a different probe and guide body to actuator 100.

Forming gib 104 and locating gib 115 may be slidably moved in directions 114 and 124 by respective pneumatic pistons 142 and 144 which are respectively coupled to forming gib 104 and locating gib 115 at operating end portions 143 (shown in FIG. 5 for forming gib 104 only) of each gib. Sliding the gibs 104 and 115 back and forth to cause the forming bar 66 and locating bar 88 to respectively move between retracted positions and locating or inspection positions may also be accomplished by using hydraulic cylinders, reversible motors and drive screws or the like.

Figure 8A:
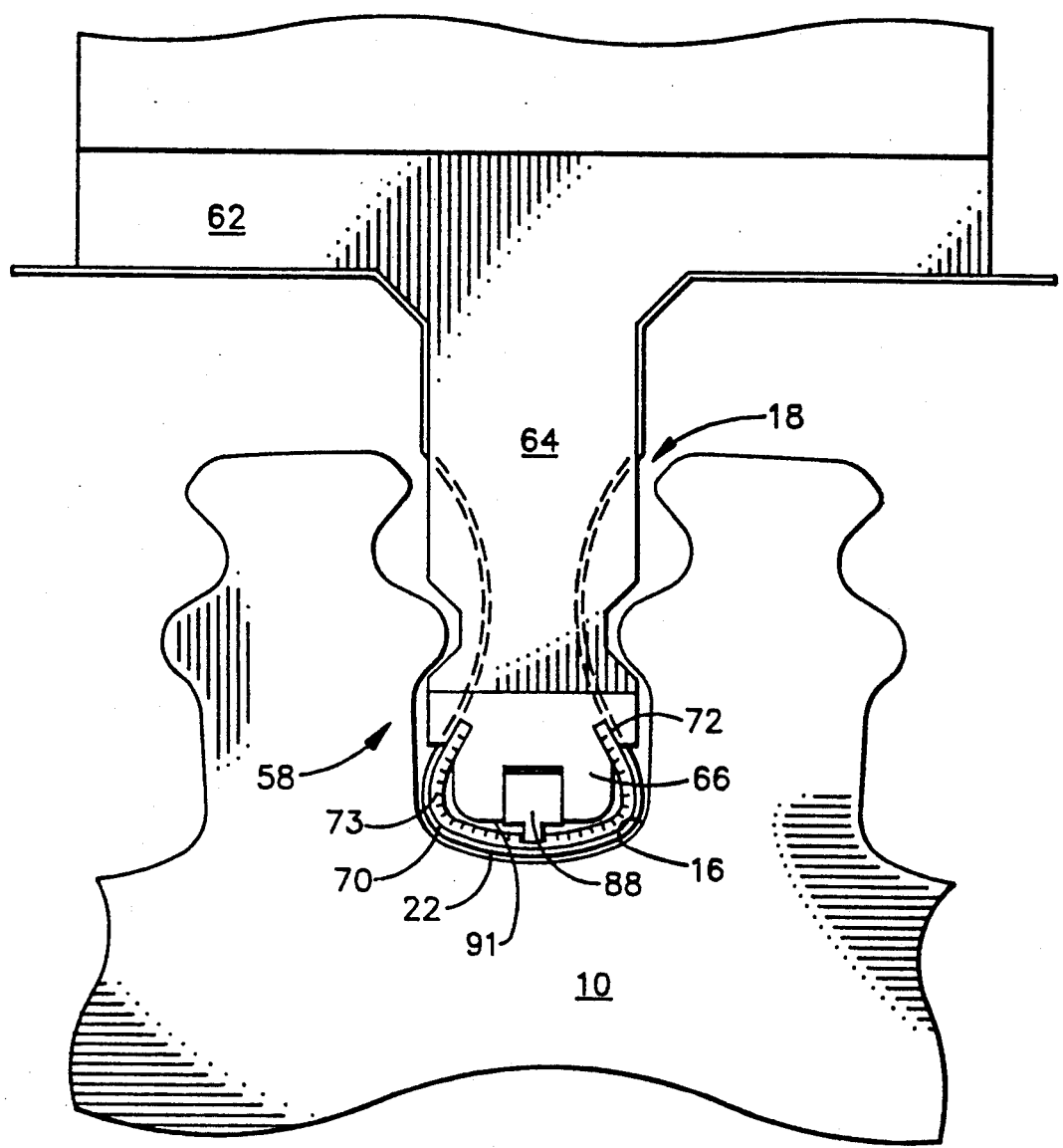
FIGS. 8A-8C illustrate the operation of the eddy current array probe device of FIG. 4.
Figure 8B:
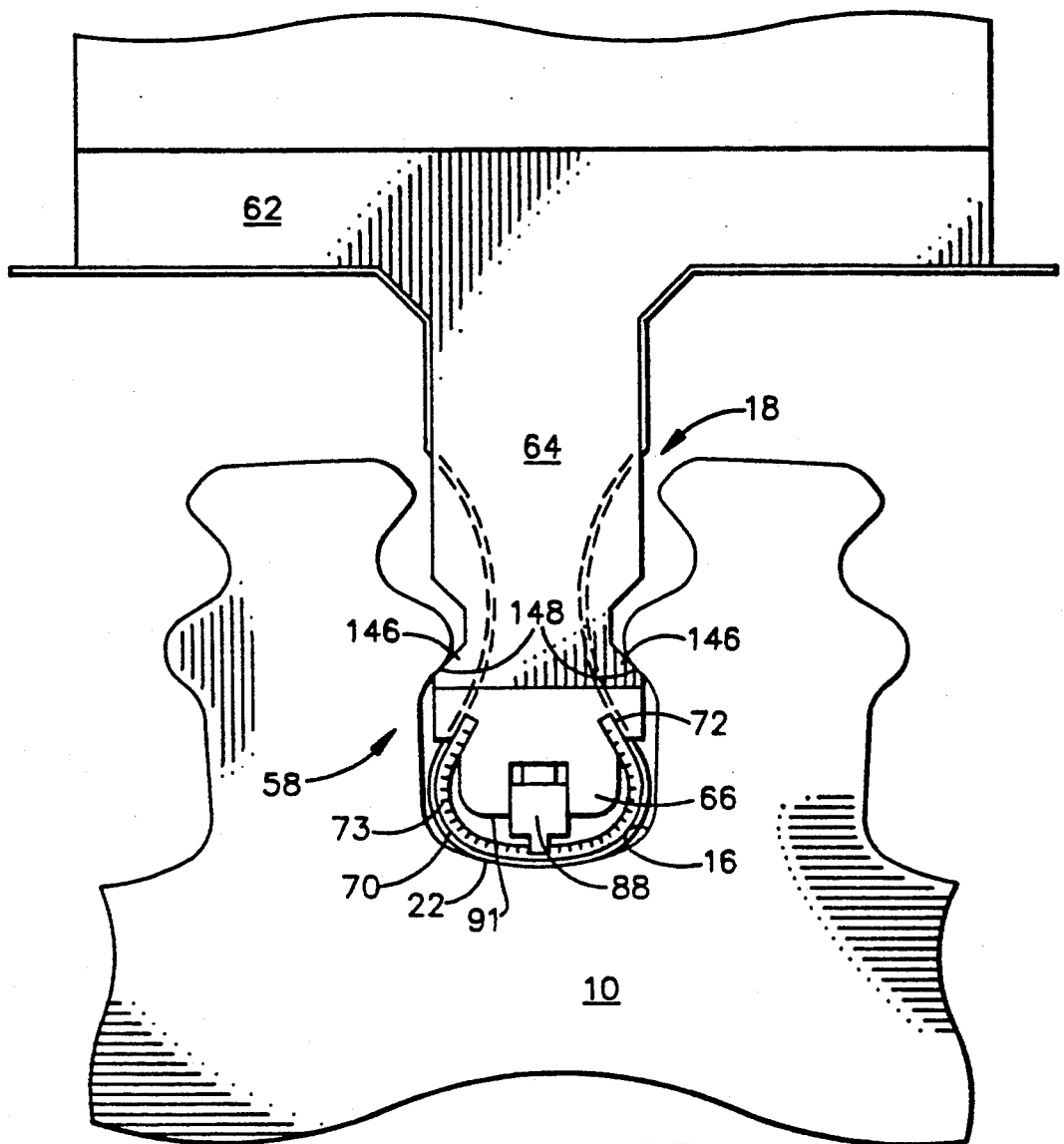
Figure 8C:
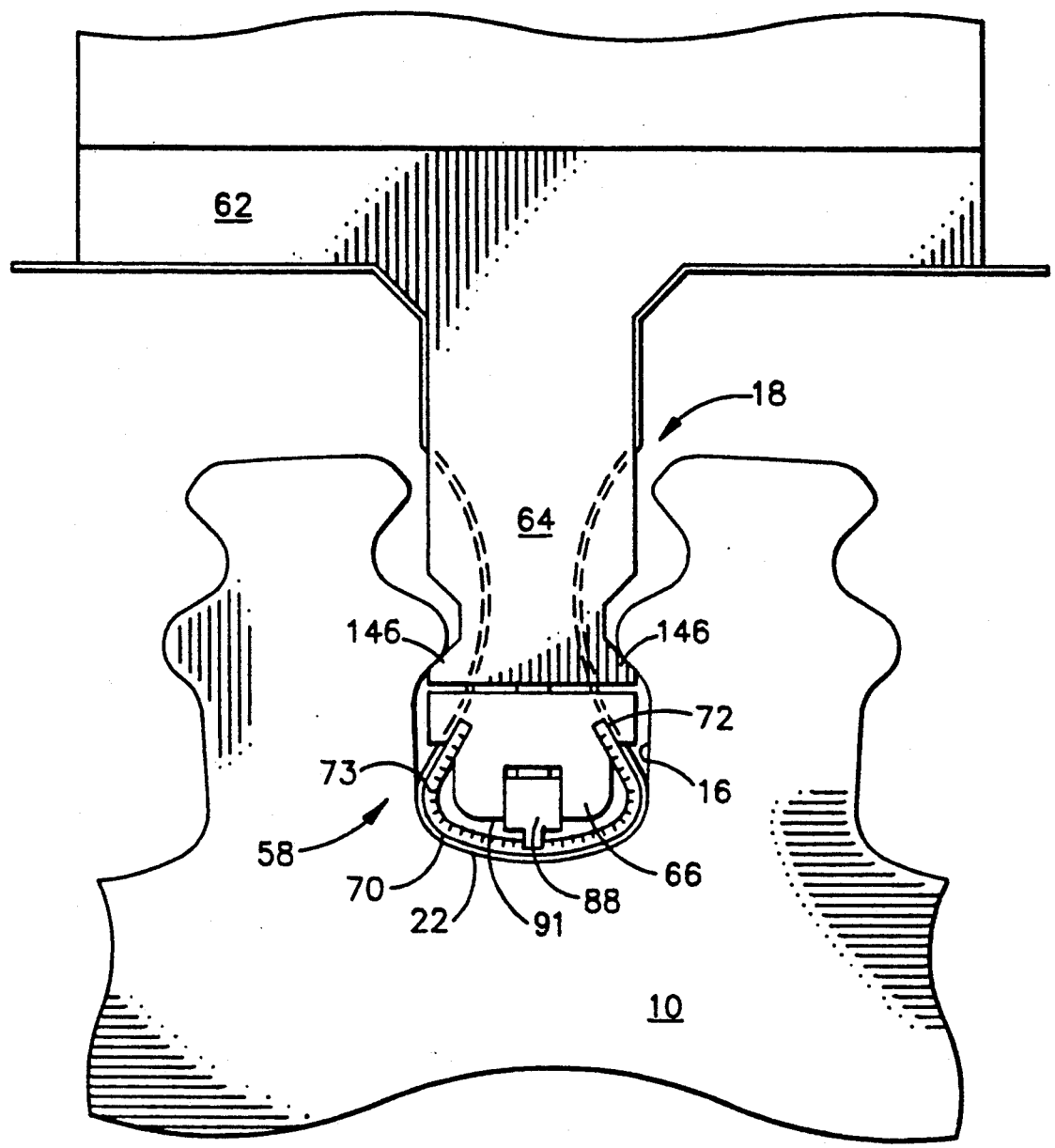

Referring to FIGS. 8A-8C, as an example of the operation of the eddy current array probe device 58 for inspecting a dovetail slot 18 of a gas turbine engine component 10, the device 58 is positioned in the dovetail slot 18 with the forming bar 66 and locating bar 88, if required, in their retracted positions. Referring to FIG. 8B, locating bar 88 is extended to its locating position to contact the base of dovetail slot 18 and shoulders 146 of guide body extension member 64 will engage lands 148 of dovetail slot 18 to properly position eddy current array circuit 22 within dovetail slot 18. Referring now to FIG. 8C, forming bar 66 is extended to its inspection position at a spacing from guide body probe extension member 64 to cause the flexible, compliant backing 70 and eddy current array circuit 22 to conform substantially to the shape of dovetail slot 18 and to maintain drive elements 26 and sense elements 28 (not shown in FIGS. 8A-8C) at respective constant equal distances from the interior surface 16 of dovetail slot 18 as the array circuit 22 is scanned through the slot 18 in a direction normal to the view shown in FIG. 8C, preferably at a controlled rate of scan. The forming bar 66 and locating bar 88 would then be retracted to their original positions to permit removal of the array probe device 58 from the dovetail slot 18 and permit insertion into another dovetail slot for inspection thereof.

Figure 9:
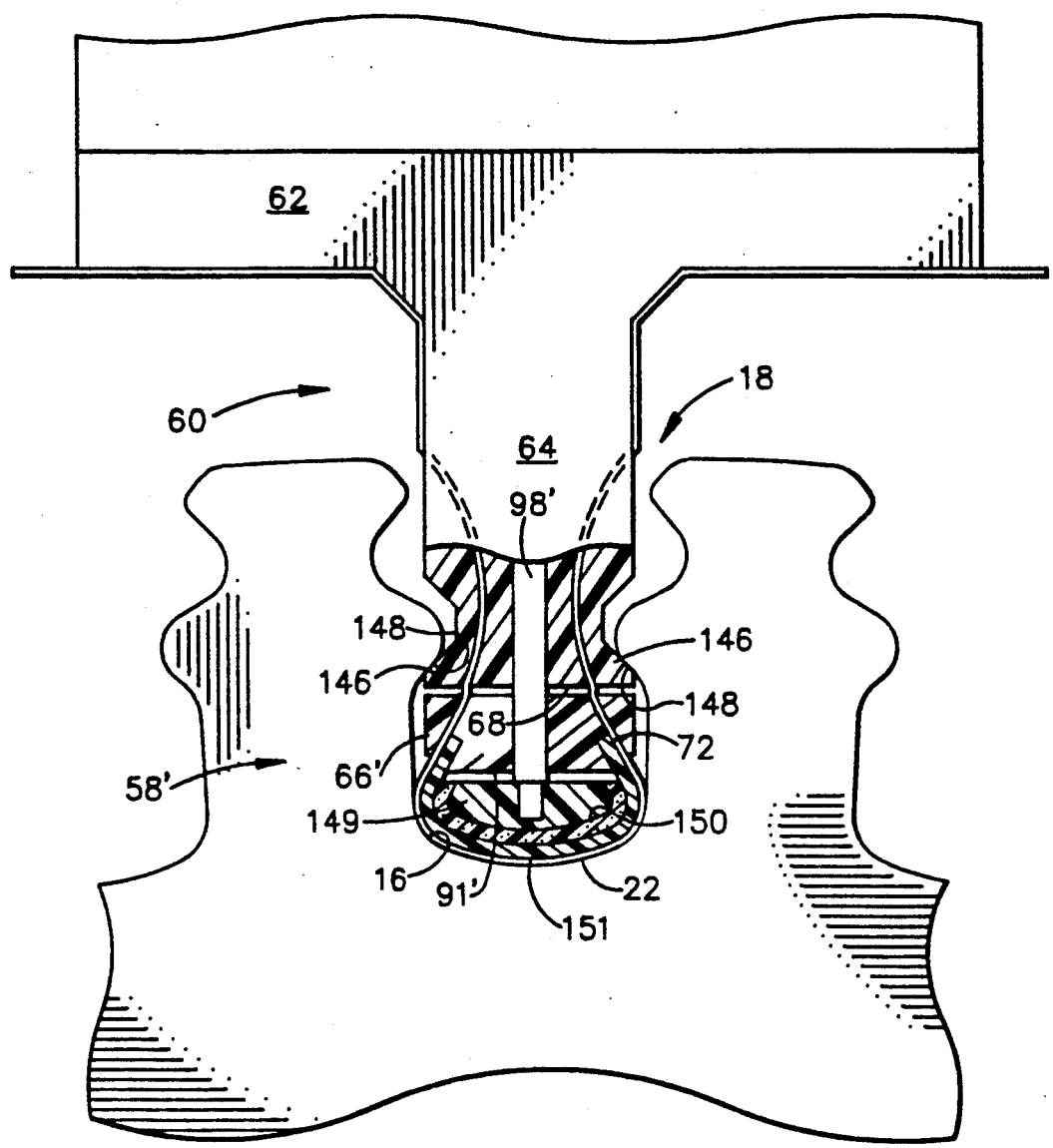
FIG. 9 is a detailed side elevation view of an eddy current array probe inspection device in accordance with another embodiment of the present invention.

Referring to FIG. 9, in accordance with another embodiment of the present invention, a device 58' includes a guide body 60 with a guide body base 62 and a guide body probe extension member 64 which are the same as those previously described. A primary forming bar 66' is positioned at an end 68 of probe extension member 64 and is movable between a retracted position against the extension member 64 and an inspection position at a spacing from the extension member 64, as shown in FIG. 9, to cause shoulders 146 of guide body extension member 64 to engage lands 148 of dovetail slot 18 to properly position eddy current array circuit 22 within dovetail slot 18. A secondary forming bar 149 is positioned at the end 91' of primary forming bar 66' and is also movable between a retracted position against the primary forming bar 66' and an inspection position at a spacing from the primary forming bar 66' as shown in FIG. 9. The secondary forming bar 149 is independently movable relative to primary forming bar 66' and is moved between its retracted and inspection positions by a pin 98' which is similar to the locating pin 98 of the previously described embodiment of the present invention. The primary forming bar 66' and secondary forming bar 149 are moved between their respective retracted and inspection positions by the actuator 100 (not shown in FIG. 9 for purposes of clarity) in the same way as forming bar 66 and locating bar 88 are moved as described hereinabove with reference to FIGS. 8A-8C. Device 58' further includes an inner backing 150 and an outer backing 151 disposed over the inner backing 150. The outer backing 151 extends over the inner backing 150 and secondary forming bar 149 and is captured within recesses 72 formed in the outer edges of the forming bar 66'. The eddy current array circuit 22 is disposed over the outer backing 151. A sacrifical layer (not shown in FIG. 9 for purposes of clarity) of material, such Kapton TM, Teflon TM or the like, may be disposed over array circuit 22 to protect and facilitate sliding of the array circuit 22 as it is moved along or scans the surface portion 16 under inspection. The inner and outer backing layers 150 and 151 and the array circuit 22 may be attached to each other by a suitable adhesive, bonding or the like to maintain proper registration and orientation of the constituents. Inner backing 150 is preferably a flexible, compressible material, such as a soft elastomeric material, an open or closed cell foam or the like, for applying a uniform pressure behind the array circuit 22 and against the inspection surface 16 to maintain the array elements at their substantially constant respective distances from the inspection surface 16 when the primary and secondary forming bars 66' and 149 are extended to their respective inspection positions during an inspection operation and thereby preventing liftoff or separation of the array circuit 22 from the inspection surface 16. The outer backing 151 may be a hard plastic with a thickness between about 0.0010" and about 0.020", which is premoldable to the expected near net shape of the inspection surface 16 to cause the array circuit 22 to conform to the inspection surface 16. An alternative is to use a compliant material for outer backing 151 similar to the backing 70 as described with respect to FIGS. 8A-8C. The outer backing 151 may also be made from a ferrite material or another layer of ferrite material may be disposed between array circuit 22 and the backing 151 to concentrate the electromagnetic flux from the drive coils 26 (not shown in FIG. 9) into the component under inspection. As previously described, the ferrite material would be a soft ferrite and preferably would have a relative permeability of 4 or more.

Figure 10:
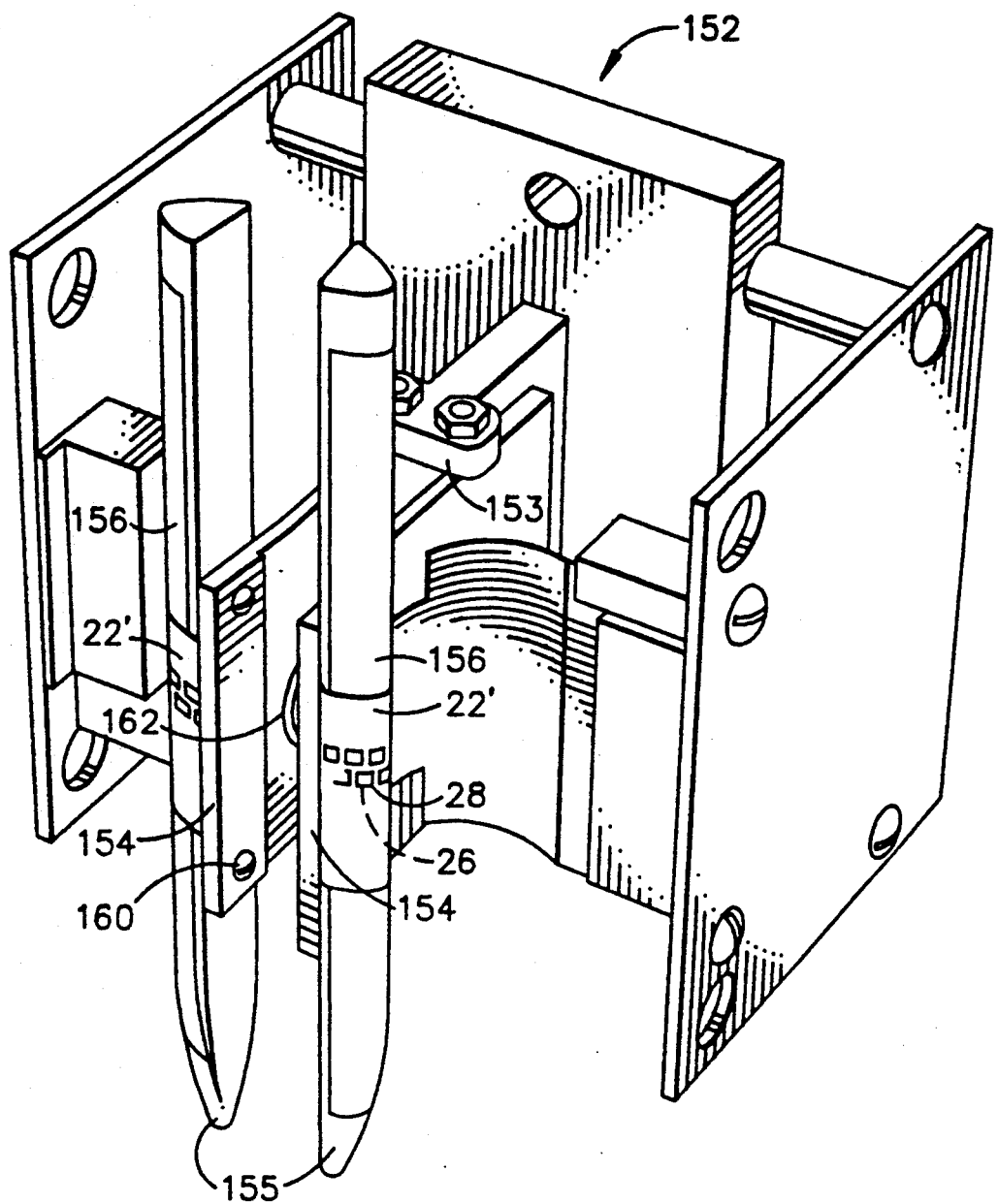
FIG. 10 is a perspective view of another embodiment of the present invention for inspecting the intermediate surface areas of a dovetail slot in accordance with the present invention.

Referring to FIG. 10, in accordance with a further embodiment of the present invention, a device 152 for inspecting an upper portion 52 (FIG. 3) of a dovetail slot 18 includes a pair of spaced base pivots 153 and a pair of facing plate members 154 each respectively hinge mounted between the base pivots 153. A pair of array support members 155 are respectively mounted to plate members 154. The array support members 155 are shaped to substantially correspond to the shape of the surface to be inspected. A hard or flexible backing 156, which may be made of a ferrite material, is integral with each of array support members 155 and a flexible eddy current array circuit 22' is disposed over each backing 156. Array circuit 22' is similar to that of array circuit 22 in FIGS. 4-6, except that array circuit 22' is split into a pair of constituents, each one being disposed over a respective backing 156 and associated support member 155. The backings 156 and array circuits 22' are each held in position at one end by clamping between corresponding support members 155 and plate members 154 by fasteners 160. Pressure, force biasing means 162 is positioned between facing plate members 154 to force array support members 155 away from each other and to engage the interior surface portion 52 (not shown in FIG. 10) of dovetail slot 18 and to maintain the drive coils 26 and sense coils or elements 28 each at a respective equal distance from the dovetail slot surface portion 52 under inspection as the array circuit 22' is scanned across the surface portion 52.

Figure 11:
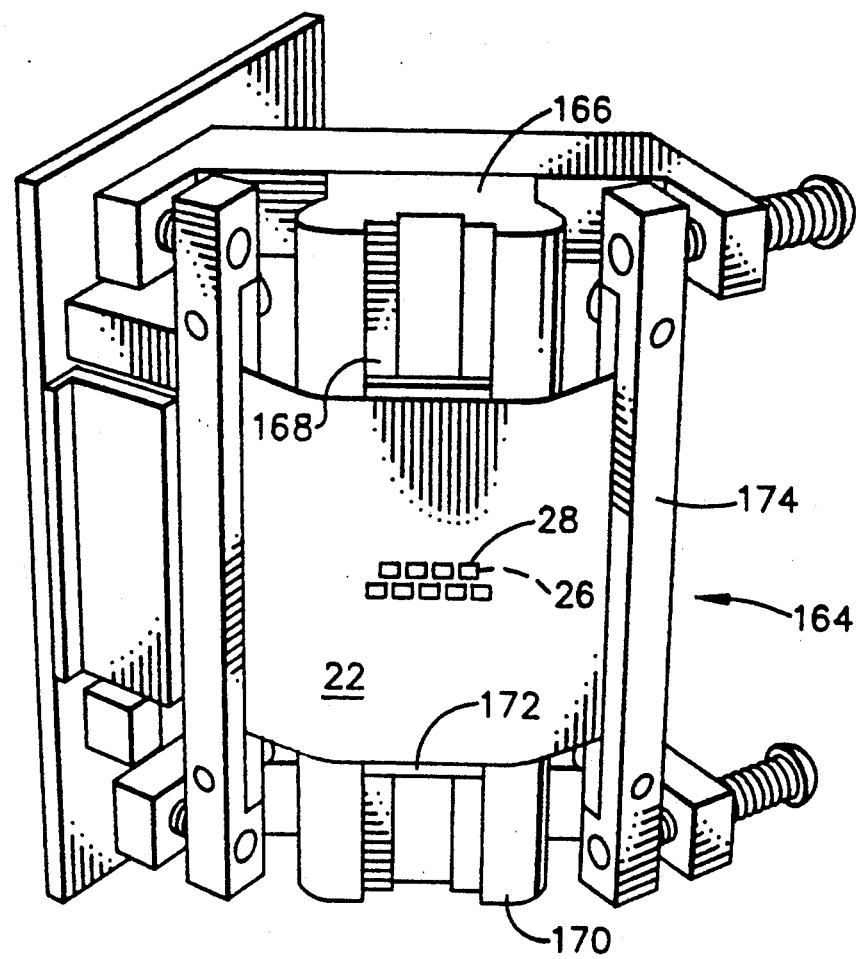
FIG. 11 is a perspective view of an eddy current array probe device in accordance with a further embodiment of the present invention for inspecting a substantially flat surface.

A further embodiment of the present invention for inspecting a substantially flat surface is shown in FIG. 11. Inspection device 164 includes an array support member 166 which may be made of a hard engineering plastic or the like. A groove 168 may be formed in an operating face 170 of inspection device 164 for receipt and retention of a backing 172. The eddy current array circuit 22 is then disposed over the backing 172 of inspection device 164 and may be held in position by suitable means, such as clamp members 174. The operating face 170 can then be positioned on a surface to be inspected and scanned across the surface to detect any defects. The backing 172 is preferably a resilient, slightly compressible material such as a foam and extends slightly above the operating face 170 to provide uniform pressure behind the array circuit 22 to force the array against an inspection surface (not shown in FIG. 11) so as to minimize liftoff or separation of the operating face 170 from the inspection surface and to maintain the drive and sense coils 26 and 28 (also not shown in FIG. 10) of array circuit 22 at a respective substantially constant distance from the inspection surface during an inspection operation. At least that portion of the backing 172 which contacts the back side of the array circuit 22 may be a soft magnetic ferrite material to direct or concentrate an electromagnetic flux from the drive coils 26 into the component under inspection when each of the drive elements 26 or coils is energized.

While the present invention has been described primarily with application to inspecting dovetail slots of a gas turbine engine component, those skilled in the art will recognize that the principles of the present invention and probe systems described can easily be modified or adapted to inspect any component with a surface having a simple or complex geometric shape. Therefore, it will be readily understood by those skilled in the art that the present invention is not limited to the specific embodiments described and illustrated herein. Different embodiments and adaptations besides those shown herein and described as well as many variations, modifications and equivalent arrangements will now be apparent or will be reasonably suggested by the foregoing specification and drawings, without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A device for inspecting a component, comprising:
    an eddy current array circuit having respective pluralities of drive and sense elements disposed on at least one flexible substrate and having an active face for positioning on a surface portion of the component during an inspection operation;
    a flexible backing layer disposed on a face of said eddy current array circuit opposite to said active face for applying a uniform pressure behind said array circuit to maintain the array circuit against the surface portion during the inspection operation;
    means for supporting and deploying said backing layer and said array circuit to conform to the surface portion of the component and to cause each of said respective pluralities of drive and sense elements to remain at a respective substantially constant distance from the component surface portion during the inspection operation; and
    means for electrically connecting said eddy current array circuit to an eddy current instrument.

2. The device of claim 1, wherein said backing layer is a flexible composite material comprising a particulate soft ferrite and a bonding organic elastomer to concentrate an electromagnetic flux from said eddy current array circuit into the component, when each of said plurality of drive elements is being energized and for shielding said eddy current array circuit from any extraneous electromagnetic energy.

3. The device of claim 2, wherein said ferrite material has a relative magnetic permeability of at least about 4.

4. The device of claim 2, wherein said ferrite material comprises about 50% to about 60% by volume particulate soft ferrite and the remaining volume including an elastomer, said particulate ferrite comprising:
    about 37% by molar composition MnO;

about 9% by molar composition ZnO; and about 54% by molar composition $Fe_2O_3$.

5. The device of claim 1, wherein said supporting and deploying means is a core of material shaped to substantially conform with the surface of the component under inspection.

6. The device of claim 5, wherein said core material is compressible to provide a close uniform fit between said eddy current array circuit and the surface of the component under inspection.

7. The device of claim 1, further comprising means for registering said eddy current array circuit relative to said supporting and deploying means to provide accurate location and size information of any detected defect during an inspection operation.

8. The device of claim 1, wherein said supporting and deploying means comprises:

location means for orienting said eddy current array circuit at substantially a same location relative to the component surface portion under inspection to provide repeatable and comparable inspection results for the same component surface portion, a different but similarly shaped surface portion of the same component and between similarly shaped surface portions of different components; and means for conforming said eddy current array circuit to a shape of the component surface portion under inspection and for maintaining each of said respective pluralities of drive and sensing elements at their respective substantially constant distances from the component surface while sliding said array circuit along the component surface portion to detect defects therein during an inspection operation.

9. The device of claim 8, wherein said locating means and said conforming means are a forming bar having an operating face shaped to cause said eddy current array circuit to conform to the shape of the component surface under inspection, said eddy current array circuit and said backing layer being disposed over said operating face with said array circuit active face being closest to the component surface portion.

10. The device of claim 9, wherein said layer has a plurality of longitudinal ridges formed therein in a face thereof adjacent to said forming bar to facilitate disposition of said backing means and said array circuit over said operating face and to prevent liftoff of said array circuit while sliding said array circuit along the component surface.

11. The device of claim 1, further comprising a sacrificial layer of material disposed over said array circuit active face to prevent wear of said active face and to facilitate sliding of said active face along the component surface portion during an inspection operation.

12. A device for inspecting a dovetail slot of a gas turbine engine component, comprising;

an eddy current array circuit having respective pluralities of drive and sense elements disposed on at least one flexible substrate and having an active face for positioning on a surface of the dovetail slot during an inspection operation;

a flexible backing layer disposed on a face of said eddy current array circuit opposite to said active face for applying a uniform pressure behind said array circuit to maintain the array circuit against the dovetail slot surface during the inspection operation;

means for supporting and deploying said backing layer and said array circuit to conform to the surface of the dovetail slot and to cause each of said respective pluralities of drive and sense elements to each remain at a respective substantially constant distance from the dovetail slot surface during the inspection operation; and means for electrically connecting said eddy current array circuit to an eddy current instrument.

13. The device of claim 12, wherein said backing layer is a soft magnetic ferrite material having a relative magnetic permeability of at least 4.

14. The device of claim 12, wherein the supporting and deploying means is a core of material shaped to substantially conform with the dovetail slot surface under inspection.

15. The device of claim 14, wherein said core material is compressible to provide a close uniform fit between said eddy current array circuit and the dovetail slot surface under inspection.

16. The device of claim 12, wherein said supporting and deploying means comprises:

a guide body having a guide body base and a guide body extension member extending from said base;

a forming bar positioned at an end of said extension member opposite to said base and movable between a retracted position against said extension member and an inspection position at a spacing from said extension member end, said forming bar having an operating face and said array circuit and said backing layer being disposed over said operating face, said operating face being shaped to cause said eddy current array circuit to conform to a shape of the dovetail slot surface under inspection when said forming bar is in said inspection position within a dovetail slot; and means for moving said forming bar between said retracted position and said inspection position to position said array circuit at substantially a same location relative to the dovetail slot surface under inspection when said forming bar is in said inspection position to provide repeatable and comparable inspection results for different dovetail slots, and to cause said array circuit to conform to the shape of the dovetail slot surface and to maintain each of said pluralities of drive and sense elements at their respective substantially constant distances from the dovetail slot surface during the inspection operation.

17. The device of claim 16, wherein said forming bar moving means comprises:

a plurality of forming pins each extending through a respective one of a plurality of channels formed through said guide body and each coupled to said forming bar; and actuator means for extending and retracting each of said plurality of forming pins to cause said forming bar to move between said retracted position and said inspection position.

18. The device of claim 17, wherein said actuator means comprises:

a housing;

an elongated forming gib slidably mounted within said housing and having a pair of substantially sawtooth shaped surfaces on opposite sides thereof to form a plurality of paired, inclined surface portions along the elongated extent of said gib;

a plurality of substantially C-shaped forming pin operating members each disposed about one of said paired, inclined surface portions and each coupled to one of said plurality of forming pins to cause each of said forming pins to extend and retract when said forming gib is respectively slid in one direction corresponding to its elongated extent and in an opposite direction; and means for sliding said gib between said one direction and said opposite direction.

19. The device of claim 18, further comprising means for readily attaching and detaching said actuator means and said supporting and deploying means to permit attachment of a different supporting and deploying means.

20. The device of claim 18, wherein said sliding means is a pneumatically operated cylinder coupled to an end portion of said forming gib.

21. The device of claim 18, further comprising:

a locating bar movable between a retracted position adjacent to said forming bar operating face and a locating position extending from said operating face; and means for moving said locating bar between said retracted position and said locating position to position said array circuit at substantially a same location relative to the dovetail slot surface under inspection when said locating bar is in said locating position, to provide repeatable and comparable inspection results for different dovetail slots.

22. The device of claim 21, wherein said locating bar moving means comprises:

a plurality of locating pins each extending through a respective one of a second plurality of channels formed through said guide body and said forming bar and each coupled to said locating bar; and said actuator means extends and retracts each of said plurality of locating pins to cause said locating bar to move between said retracted position and said locating position.

23. The device of claim 22, wherein said actuator means further comprises:

an elongated locating gib slidably mounted within said housing and having a pair of substantially sawtooth shaped surfaces on opposite sides thereof to form a plurality of paired, inclined surface portions along the elongated extent of said locating gib;

a plurality of substantially C-shaped locating pin operating members each disposed about one of said paired, inclined surface portions and each coupled to one of said plurality of locating pins to cause each of said locating pins to extend and retract when said locating gib is respectively slid in one direction corresponding to its elongated extent and in an opposite direction; and means for sliding said gib between said one direction and said opposite direction.

24. The device of claim 23, wherein said sliding means is a pneumatically operated cylinder coupled to an end portion of said forming gib.

25. The device of claim 16, further comprising:

a locating bar movable between a retracted position adjacent to said forming bar operating face and a locating position extending from said operating face; and means for moving said locating bar between said retracted position and said locating position to position said array circuit at substantially a same location relative to the dovetail slot surface under inspection when said locating bar is in said locating position, to provide repeatable and comparable inspection results for different dovetail slots.

26. The device of claim 12, wherein said eddy current array circuit is formed in a pair of array circuits and said backing layer is formed in a pair of backing means;

said supporting and deploying means, comprising:

a pair of array circuit support members each shaped to matingly fit the surface under inspection, one of said pair of backing layer being disposed over each of said support members and one of said pair of array circuits being disposed over each of said backing layer and over each of said support members;

a base member, each of said pair of support members being pivotably mounted for movement to said base member in opposed spaced relation;

biasing means for urging each of said support members and said array circuit associated with each support member into close uniform contact with the surface under inspection to cause each of said respective pluralities of drive and sense elements to remain at their respective substantially constant distances from the surface under inspection during a scanning operation.

27. The device of claim 26, wherein said biasing means urges said support members away from each other.

28. The device of claim 26, wherein said biasing means urges said support members toward each other.

29. The device of claim 26, further comprising registration means for properly orienting said array circuit relative to said support member to provide repeatable and comparable results between inspections of different surfaces.

30. The device of claim 26, wherein at least a portion of each of said pair of backing means behind each of said pair of array circuits is a magnetic ferrite containing material.

31. A device for inspecting a component, comprising:

an eddy current array circuit having respective pluralities of drive and sense elements disposed on at least one substrate and having an active face for positioning on a surface of the component during an inspection operation;

outer backing means disposed on a face of said eddy current array circuit opposite to said active face for supporting said eddy current array circuit, said outer backing means being premoldable to conform substantially to a near net shape of the surface to be inspected to cause said array circuit to conform to the near net shape of the inspection surface;

inner backing means disposed on a face of said outer backing means opposite to said eddy current array circuit, said inner backing being a pliable, compressible material for providing uniform pressure behind said array circuit when in contact with the inspection surface; and means for supporting and deploying said inner and outer backing means and said array circuit against the inspection surface during the inspection operation; and means for electrically connecting said eddy current array circuit to an eddy current instrument.

32. The device of claim 31, wherein said supporting and deploying means comprises:

a guide body having a guide body base and a guide body extension member extending from said base;

a primary forming bar positioned at an end of said extension member opposite to said base and movable between a retracted position against said extension member and an inspection position at a spacing from said extension member end to properly position said array circuit and said inner and outer backing means relative to the inspection surface;

a secondary forming bar positioned at an end of said primary forming bar opposite to said extension member and movable between a retracted position against said primary forming bar and an inspection position at a spacing from said primary forming bar to cause said array circuit to contact and conform to the inspection surface; and means for moving said primary and secondary forming bars between their respective retracted and inspection positions.

33. A device for inspecting a component, comprising:

an eddy current array circuit having respective pluralities of drive and sense elements and having an active face for positioning on a surface portion of the component during an inspection operation;

backing means disposed on a face of said eddy current array circuit opposite to said active face for applying a uniform pressure behind said array circuit to maintain the array circuit against the surface portion during the inspection operation; and means for supporting and deploying said backing means and said array circuit to conform to the surface portion of the component and to cause each of said respective pluralities of drive and sense elements to remain at a respective substantially constant distance from the component surface portion during the inspection operation, said supporting and deploying means including a support member having an operating face and a groove formed in said operating face for receipt and retention of said backing means; and means for electrically connecting said eddy current array circuit to an eddy current instrument.

34. The device of claim 33, wherein said backing means is a resilient, compressible material and extends slightly above said support member operating face to cause the array circuit to remain in contact with the surface portion during an inspection operation.

35. The device of claim 34, wherein at least a portion of said backing means immediately behind said array circuit is a magnetic ferrite containing material.

* * * * *